United States Patent [19]
Gander

[11] 4,062,451
[45] Dec. 13, 1977

[54] LAMINATED STRUCTURES COMPRISING FILMS OF SILANE CROSSLINKED ACRYLATE INTERPOLYMERS HAVING WATER BARRIER PROPERTIES

[75] Inventor: Robert J. Gander, Whitehouse, N.J.

[73] Assignee: Johnson & Johnson, New Brunswick, N.J.

[21] Appl. No.: 645,062

[22] Filed: Dec. 29, 1975

Related U.S. Application Data

[60] Division of Ser. No. 505,414, Sept. 12, 1974, Pat. No. 3,951,893, which is a continuation-in-part of Ser. No. 90,539, Nov. 18, 1970, abandoned.

[51] Int. Cl.$^2$ .................. B32B 3/02; A61F 13/16; B65D 81/02
[52] U.S. Cl. .................. 206/524.2; 128/283; 128/294; 428/286; 428/332; 428/192; 428/447; 428/913; 428/35; 526/279; 220/65
[58] Field of Search ........... 428/447, 913, 266, 332, 428/192, 286; 526/279; 260/23 AR, 46.5 UA, 827; 220/65; 206/524.2

[56] References Cited
U.S. PATENT DOCUMENTS

| | | | |
|---|---|---|---|
| 3,480,016 | 11/1969 | Costanza et al. | 428/302 |
| 3,617,362 | 11/1971 | Bemmels et al. | 526/279 |
| 3,706,697 | 12/1972 | Backderf | 526/279 |
| 3,716,399 | 2/1973 | Nitzsche et al. | 428/447 |

FOREIGN PATENT DOCUMENTS

1,127,625  9/1968  United Kingdom.

*Primary Examiner*—George F. Lesmes
*Assistant Examiner*—William R. Dixon, Jr.

[57] ABSTRACT

Polymeric compositions having desirable film-forming characteristics and water-barrier properties at substantially neutral pH's and yet solubilizable and thus disposable at substantially non-neutral pH's comprise a silane crosslinked interpolymer of an alkyl acrylate and a monomer interpolymerizable therewith such as, in the preferred alkaline labile embodiment, acrylic acid. The silane crosslinking monomer is preferably 3-(trimethoxysilyl)-propyl methacrylate or 3-(trimethoxysilyl)-propyl acrylate. The resultant pH-sensitive polymeric compositions in film form, are laminated to other dispersible materials to produce a variety of products which are completely disposable at selected non-neutral pH's.

16 Claims, 10 Drawing Figures

LAMINATED STRUCTURES COMPRISING FILMS OF SILANE CROSSLINKED ACRYLATE INTERPOLYMERS HAVING WATER BARRIER PROPERTIES

CROSS-REFERENCE TO RELATED APPLICATION

This application is a division of my copending application Ser. No. 505,414, filed Sept. 12, 1974, now U.S. Pat. No. 3,951,893 which application is, in turn, a continuation-in-part of application Ser. No. 90,539, filed Nov. 18, 1970, now abandoned.

BACKGROUND OF THE INVENTION

1. Field of the Invention

The present invention relates to polymers and methods of producing the same, the polymers having film-forming characteristics and the films produced therefrom having water-barrier properties at substantially neutral pH's and yet being substantially completely solubilizable at non-neutral pH's. More particularly, the invention relates to silane-crosslinked interpolymers of alkyl acrylates and, in a preferred embodiment, acrylic acid, and disposable products produced therefrom.

While the composition and products of the present invention are herein described primarily in connection with advantageous applications in the medical and sanitary product fields, it should be understood that the present invention is not limited thereto. In the light of the present disclosure, those skilled in the art will recognize a variety of applications in other fields wherein the moisture impermeability and film-forming characteristics of the alkaline-labile or acid-labile silane-crosslinked polymers of the present invention may be advantageously employed.

2. Description of the Prior Art

There has long been a need in the handling of waste products of the liquid or semi-liquid type, such as body exudates, to have a material which would contain the waste when excreted but which could then be readily disposed of later. In hospital use, for example, there are bedpans, urinals, emesis basins, bags for wound irrigation, bags for incision and drainage of abscesses, bags for urine collection, bags for ostomies, i.e., ileostomies, colostomies, etc., and other containers which are used daily for the collection of body exudates in a liquid or semi-liquid form. Similarly, in home use, body exudates are collected in bandages, pads, diapers and similar sanitary products. The problem of convenient, sanitary, esthetic and inexpensive disposal is ever present.

One prior art approach has been to utilize various plastic materials, such as polyethylene, to form water-impervious containers, barriers or liners for collection of the body exudates. The waste material and the plastic film can then be dropped into a toilet bowl and the liquid or semi-liquid waste flushed away. But the problem of disposal of the plastic film, which is not soluble, still exists. The film can not be flushed away without ultimately causing plumbing and sewage treating problems. Instead, it is retained and collected in containers, the contents of which are later incinerated or dumped into a trash disposal area. Quite aside from the esthetic problem and the attendant inconvenience and cost, the practice is undesirable from the standpoint of possible spread of contamination or disease.

Another prior art approach is described in U.S. Pat. No. 3,480,016, issued Nov. 25, 1969, and entitled "Sanitary Products". This patent discloses, for example, toilet-flushable sanitary products comprising biodegradable fibers bonded together by a resin. The resin is stable to body discharges which have pH's ranging from about 4.6 to about 8.4, but is solubilizable under selected acid or alkaline conditions substantially outside this range. The polymers employed, however, are unduly hydrophilic in nature and in practice do not form films having true moisture-barrier properties. Accordingly, while the polymers, as well as associated absorbent materials, can be disposed of along with the waste material by solubilizing the same, certain applications require the presence of a supplementary moisture barrier, thus rendering the product not truly disposable in its entirety and complicating the disposal problem, as already described. That is, the polymers described in U.S. Pat. No. 3,480,016 are not crosslinked in any manner and are not suitable for forming films with water barrier properties, but can only be used as binders for "sanitary products".

British Pat. No. 1,127,625 discloses generally the use of alkoxy-silyl-alkyl monomers as crosslinking agents for polymers such as acrylate polymers for pressure-sensitive adhesives. This patent, however, contains no suggestion either of producing films having water-barrier properties at neutral pH's that are also solubilizable in aqueous media at substantially non-neutral pH's, nor of the particular silane monomers and proportions thereof that I have found to be critical, in accordance with the present invention, for producing polymers from which such films can be manufactured.

OBJECTS OF THE INVENTION

It is therefore a general object of the present invention to cope with these and other problems of the prior art. It is another general object to provide a polymeric composition having desirable film-forming characteristics and water-barrier properties at substantially neutral pH's and yet being solubilizable at substantially non-neutral pH's. It is another general object to avoid the hydrophilic nature of prior-art pH-sensitive films and to provide polymeric films having water-barrier characteristics at substantially neutral pH's, said films being otherwise solubilizable at substantially non-neutral pH's.

It is a specific object of the present invention to provide sanitary products, including bags, vessels, liners, pads and the like, which contain or otherwise hold body exudates and have water-barrier properties at neutral pH's so as to prevent seepage or leakage but are otherwise completely dispersible or solubilizable at substantially non-neutral pH's. It is another specific object of a preferred embodiment of the invention to provide a polymeric composition having water-barrier properties at pH's substantially below about 9 and yet being completely solubilizable at pH's substantially above about 9.

It is a still further object to provide composite or laminated sanitary products from pH-sensitive, water-impermeable, heat-sealable thermoplastic polymers in combination with other water dispersible materials to form completely disposable sanitary products. These and other objects of the present invention will become apparent as the detailed description proceeds.

SUMMARY OF THE INVENTION

These objects are achieved in a particular embodiment by providing a polymeric composition comprising a silane crosslinked interpolymer of certain ethylenically unsaturated monomers herein set forth. The silane crosslinking agent attenuates the hydrophilic nature of the interpolymer and imparts the desired water barrier properties to the films produced therefrom at substantially neutral pH's, e.g., pH's in the range of about 4.5 to about 8.5. Yet, in substantially alkaline or acid solutions, the polymeric composition is completely solubilizable and thus conveniently disposable.

DESCRIPTION OF THE PREFERRED EMBODIMENTS

The Interpolymer

The interpolymer is made up of a first monomer selected from the group consisting of alkyl acrylates, the alkyl group having one to eight carbon atoms, e.g., methyl acrylate, ethyl acrylate, etc., preferably ethyl acrylate, and a second monomer which is selected to achieve the particular alkaline or acid labile characteristic desired. In the preferred alkaline labile embodiment, wherein the polymeric composition is solubilizable in aqueous alkaline solutions having pH's substantially above about 9, e.g., 10 or higher, usually 12 or higher, the second monomer is an acid comonomer selected from the group consisting of acrylic acid, methacrylic acid, fumaric acid, maleic acid, maleic anhydride and itaconic acid. The preferred acid comonomer is acrylic acid. In the acid labile embodiment, wherein the polymeric composition is solubilizable in acidic solutions having pH's substantially below about 4.5, i.e., pH's of 4 or lower, the second monomer is selected from the group consisting of dimethylaminoethyl acrylate, dimethylaminoethyl methacrylate, diethylaminoethyl acrylate, diethylaminoethyl methacrylate, tert.-butylaminoethyl acrylate and tert.-butylaminoethyl methacrylate, and is preferably dimethylaminoethyl methacrylate. It will, of course, be understood that mixtures of each of the foregoing groups of monomers may be used.

The proportions of the first monomer and second monomer depend in part upon the particular monomers employed and the characteristics desired in the resulting silane crosslinked interpolymer. In general, the first monomer is present in the proportion of about 0.5 to 5 parts by weight per part of second monomer, preferably about 1.5 to 4 parts by weight per part of second monomer. Within these ranges the proportions may be varied to impart desired characteristics. For example, increasing the proportion of methacrylic acid or acrylic acid, which are hardening monomers, increases the rate at which the interpolymer dissolves in non-neutral solutions, but also decreases flexibility, and vice versa.

Similarly, the particular selection of monomers employed can significantly affect properties. For example, the longer chain alkyl acrylates impart greater flexibility to the resulting film but also increase tackiness and decrease the rate at which the film will dissolve in non-neutral solutions. Likewise, the use of methacrylic acid instead of acrylic acid produces a stiffer interpolymer.

The Crosslinking Monomers

The essential crosslinking monomers contain both an ethylenic linkage and an alkoxysilyl or acyloxysilyl group. These monomers interpolymerize through their ethylenic linkages, thereby becoming incorporated in the interpolymer backbone. The polymers remain linear, soluble and uncrosslinked until crosslinking is made to take place through reaction of the alkoxysilyl or acyloxysilyl groups pendant from the polymer backbone, as hereinafter set forth.

Various crosslinking monomers of the above mentioned type have been used, including 3-(trimethoxysilyl)-propyl acrylate, 3-(trimethoxysilyl)-propyl methacrylate, allyl trimethoxysilane, vinyl triethoxysilane and vinyl triacetoxysilane, as set forth in the examples hereinafter. While each of these compounds, upon crosslinking, introduces a crosslinked, solvent-insoluble gel structure into the interpolymer film, it is found that, of the above-listed crosslinking monomers, only the 3-(trimethoxysilyl)-propyl acrylate and 3-(trimethoxysilyl)-propyl methacrylate are effective in producing films with good water barrier properties.

More particularly, the crosslinking agents suitable for use in the interpolymer compositions of the present invention, of which the latter two crosslinking agents are preferred, include the silane monomers having the structural formula:

wherein:
R is selected from the group consisting of $CH_3-$, $CH_3CH_2-$, $CH_3O-$ and $CH_3CH_2O-$;
$R_1$ and $R_2$ are each selected from the group consisting of $CH_3-$ and $CH_3CH_2-$;
$R_3$ is selected from the group consisting of $H-$, $CH_3-$ and $CH_3CH_2-$; and $n$ is 0 or a positive integer not greater than 8.

Since the number of crosslinks obtained in the polymeric composition is proportional to the concentration of silane monomer used therein, at least about 0.7% by weight, based upon the combined weight of the first and second monomer, of the crosslinking agent should be employed to achieve the desired water barrier property. Concentrations substantially less than 0.7%, e.g., 0.25% and 0.5%, have resulted in unsatisfactory water barrier properties. The upper concentration limit for the silane crosslinking agent is in the range of from about 2 to 3%, amounts substantially in excess thereof causing instability and undesired gelation during polymerization. The preferred range is from about 0.9 to about 1.5%.

Modifying Agents

Compatible modifying agents may also be incorporated into the composition of the present invention to achieve desired product characteristics, as will be apparent to those skilled in the art. Such modifying agents must, of course, not unduly affect the basic characteristics of the interpolymer, particularly its solubility at selected pH's. Manifestly, the modifying agents must themselves also be soluble at the selected solubilizing pH's.

As an example, in the acid labile embodiment, N-isopropylacrylamide may be incorporated to decrease the surface tack of the resulting film. For such purposes, as much as about 5 to 25% by weight, based on the total weight of the polymer, may be incorporated in the composition. Similarly, to offset the tendency of the alkaline labile or acid labile silane crosslinked interpolymers to crack if repeatedly flexed under conditions of low humidity, it has been found desirable to incorporate therein about 1 to 20% by weight, based on the total weight of the polymer, preferably about 2 to 10%, of a humectant-type plasticizer. Plasticizers suitable for this purpose include glycerine, diethylene glycol, triethylene glycol, propylene glycol, dipropylene glycol and tripropylene glycol.

Still other plasticizers may be advantageously employed for particular purposes. For example, when the films of the present invention are formed by casting a solution of the polymer on a substrate, the release of the film from the substrate can be substantially facilitated by first adding to the interpolymer composition a plasticizer having release agent properties. Suitable plasticizers having release agent properties, which also dissolve readily in aqueous alkaline solutions, are the long chain monocarboxylic fatty acids, such as lauric, myristic, and palmitic acids. For such purposes, at least about 1% by weight, based on the total weight of the polymer, of the plasticizer should be employed, preferably about 2 to 10%. Since such plasticizers have no apparent undesirable effects on the water-barrier properties of the film, as much as 20% plasticizer may also be used, although such higher amounts provide no particular improvement in film properties or release characteristics.

In a preferred embodiment, both a humectant-type plasticizer and a plasticizer having release agent properties are employed. Thus, films of the present invention having excellent properties with respect to both flexibility and improved release are obtained by incorporating about 2 to 10% by weight of each type of plasticizer in the polymeric composition, e.g., 5% of glycerine and 5% of lauric acid.

Method of Preparation

The silane crosslinked polymers of the present invention may be prepared, for example, by solution polymerization of the first and second monomers, e.g., acrylic acid and ethyl acrylate, in the presence of the silane crosslinking agent, e.g., 3-(trimethoxysilyl)-propyl methacrylate. The solvent is preferably an organic solvent having a boiling point not substantially in excess of about 100°–110° C, such as, for example, ethyl acetate, toluene, benzene, methyl ethyl ketone, or the like.

In a preferred embodiment, the solvent may also include isopropanol, which has the unique property of acting both as a solvent and a stabilizing agent whereby undesired gelation of the solution is prevented. Typical proportions of solvent and points of addition will be evident from the specific examples herein.

After the first and second monomers and cross-linking agent are admixed in the solvent, the solution is stirred and swept with nitrogen, and its temperature is raised to about 75° C. A catalytic amount of a polymerization catalyst, e.g., a vinyl polymerization initiator such as 2,2'-azobis-(2-methylpropionitrile) or the like, it added and the nitrogen flow discontinued. The exothermic polymerization reaction proceeds with vigorous refluxing, the temperature rising to about 80°-90° C. After the exothermic polymerization has subsided, stirring and heating to maintain the temperature at about 80° C continues for several hours to assure substantially complete polymerization.

During the polymerization reaction, the alkoxy silane crosslinking monomer interpolymerizes with the other monomers. The crosslinking reaction does not, however, occur until the polymer solution is dried by driving off the solvent. In a preferred embodiment, wherein the product is produced in film form, the polymer solution is first diluted to a solids content of less than about 35% by weight, e.g., about 30%, and plasticizers are added. It is then spread in one or more thin coats on a release surface such as silicone-coated paper or polyethylene-coated paper with air drying between coats, drying preferably being completed at elevated temperatures, e.g., about 50° to 100° C.

The crosslinking reaction is accelerated by drying at elevated temperatures. It may also be accelerated by the presence of catalytic amounts (e.g., about 0.5% by weight, based on the weight of the interpolymer) of a catalyst known to promote certain siloxane condensation reactions. Examples of suitable accelerant catalysts are zinc, stannous, lead and iron octoates, and dialkyl tin carboxylates such as dibutyl tin dilaurate and dibutyl tin di-2-ethylhexoate.

The thickness of the film may be adjusted by varying the solids content of the solution, by varying the thickness of each layer of the deposited solution, by varying the number of layers or by a combination of these techniques, or the like. Film thicknesses are typically in the range of about 1 to 20 mils, preferably 2 to 10 mils. Because flexibility is in part a function of film thickness, the thinner-walled films are employed where a high degree of flexibility is desired. The thinner-walled films also reduce material costs.

In a dry state, the resulting films are clear, flexible and have surfaces which may be slightly cohesive. Under humid conditions, the surfaces may become more cohesive due to moisture absorption. Because the film may thus block to itself on long standing, particularly under moist conditions, it should preferably be stored with an interliner such as silicone coated paper, polyethylene or polyethylene-coated paper. As will be apparent hereinafter, the blocking problem may otherwise be coped with when the film is laminated with other nonblocking materials to form composite products.

Further specifics as to the preparation of the product of the present invention will be apparent from the examples, many details otherwise being within the skill of the art in the light of this disclosure.

Disposal Solutions

As previously indicated, the polymers of the present invention and films formed therefrom are solubilizable in aqueous alkaline or acid solutions, preferably solutions having pH's of about 12 or higher or about 3 or lower, respectively, depending on the particular embodiment. In the preferred alkaline labile embodiment, solutions of strong alkalis, such as lithium, sodium and potassium hydroxides, disintegrate and dissolve the film most rapidly, sodium hydroxide being the preferred alkali.

Sodium carbonate solutions or ammonia solutions will dissolve the film, but the rate of solution is much slower, e.g., less than half the rate. Moreover, the concentration of ammonia or sodium carbonate solutions required to dissolve the film, e.g., about 1 to 10% by weight, is higher than the concentration of sodium hydroxide solutions, e.g., about 0.5%, as will be apparent from Example 1 hereinafter.

It should be noted that solutions of divalent alkaline earth hydroxides, such as calcium or barium, are unsuitable. They interact with the carboxyl groups on adjacent chains in the polymer, further crosslinking the polymer and thus interfering with the solubilizing of the same.

In the acid labile embodiment, hydrochloric acid of 4 to 6 normal concentration (12 to 18% HCl) is the preferred solubilizing solution to obtain as rapid a break-up of the film into pieces as possible. The 4 to 6 normal concentration softens and swells the film faster than lower or higher concentrations of this acid. Even 1 normal hydrochloric acid (3% HCl) will ultimately dissolve the film completely, but its action in disintegrating the film to flushable pieces is much slower than that of 4 normal acid.

Sulfuric acid solutions at any concentration from 1 to 20 normal are much poorer than hydrochloric acid solutions for disintegrating the film. Any concentration of sulfuric acid from 2 normal up will, however, ultimately dissolve the film. Solutions of sodium acid sulfate or potassium acid sulfate do not soften or dissolve the film and are to be avoided.

In practice, the alkaline labile or acid labile interpolymers and products produced therefrom are readily disposed of by depositing the same with the waste products contained therein in a toilet bowl, adding the requisite sodium hydroxide or hydrochloric acid to achieve pH adjustment, and shortly thereafter flushing the entire contents. No messy handling is otherwise involved.

Composite Products

The thermoplastic nature of the polymeric compositions of the present invention, whether in the forms of films or otherwise, lends itself to the formation of composite products, the components of which complement one another. This is illustrated, for example, by laminating films of the present invention to fiber webs having substantially no wet strength, the resulting composite solving several problems associated with the free standing films, as described in the following paragraphs.

The rate of solution of the silane-crosslinked polymer films is dependent to some degree on the thickness of the film being used. As a result, it is highly desirable to use as thin a film as practical in making disposable products. One problem with extremely thin films, however, is that as the films become thinner the strength of the film is proportionately decreased. Even though films having excellent water barrier properties can be formed with a thickness as low as 2 mils, they are relatively weak. This problem is aggravated by adsorbed or imbibed water which acts as a plasticiser, making the film more readily extensible and thereby weaker.

A further problem is that, as aforementioned, the films are somewhat cohesive and are difficult to handle when rolled or otherwise placed together. It thus becomes necessary to use release interliners to prevent sticking.

These problems are solved by the aforementioned composite formed by laminating the film to a fiber web such as cellulosic paper. In the preferred practice, papers are used which have relatively high dry strength, for example, 100 to 200 grams/inch-width in the cross machine direction and 300 to 500 grams/inch-width in the machine direction. The preferred fiber webs have little or no wet strength and readily disintegrate and become flushable in a toilet system, as is presently done with commercially available toilet papers. Papers with greater dry strength than above indicated are preferred provided the wet strength is sufficiently low to permit flushing. Because the stiffness of the paper is incorporated into the final laminate product, relatively thin, flexible papers are preferred in those embodiments wherein flexibility is a desirable attribute.

If desired, the fibrous sheet can be formed of a web of relatively-long fibers which are randomly laid to give strength in all directions. Fibers of this type are, for example, those utilized in making non-woven fabrics, where fiber lengths of ½ inch or greater are generally used. Alternatively, the fibers may be highly "oriented" or "parallelized" to achieve desired characteristics.

In preparing the fiber-film laminate, the film is first cast from a solvent onto a release paper and then dried and cured, as previously described. While still on the carrier paper, the film is pressed into intimate contact with the fiber web while being subjected to sufficient heat and pressure to soften the film and bond the film to the web at their contacting surfaces. In forming the laminate, however, care should be used so that the film is not completely penetrated by fibers of the fiber web as this would destroy the integrity of the film and thus cause leakage in the final film-fiber laminate.

The bonded fiber web substantially increases the dry strength of the film, and also eliminates the problem of tackiness and the need for an interliner. In utilizing the film-fiber laminate for containing body exudates or other aqueous liquids, the fiber portion of the laminate is disposed exteriorly. The film thus acts as a moisture barrier and the fiber portion remains dry and retains its dry strength until deposited in a toilet bowl or the like.

If it is desired to make water-impermeable sheets which present no problem with respect to tack or tackiness, a fiber web may be laminated to both sides of the film. This may be conveniently done by passing the paper-film-paper composite between a laminating nip of heated metal rolls. The fiber web on the side of the laminate which is to be in contact with liquids is preferably light weight and of minimum stiffness. Since the web is being used only as a protective blocking layer and is wetted by the contained liquids, its dry strength is immaterial.

Another advantageous composite product application for the polymeric composition of the present invention is as a binder in the formation of water-permeable, non-woven fabric or mats. The non-woven fabric is held together in the presence of substantially neutral solutions by the polymeric composition of the present invention. The polymer may be distributed throughout the fibers. Alternatively, the polymer may be distributed in a plurality or multiplicity of discrete deposits in various shapes and binder patterns and in sufficient amounts to bind the nonwoven fabric together.

Impregnation of the non-woven fabric with the polymer may be by conventional techniques well within the skill of the art in the light of this disclosure. Patterns for binding the fabric together may include those taught in the prior art, such as in the non-woven fabrics of U.S. Pat. Nos. 2,705,687, 2,782,130 and 3,009,823.

Still another composite product of the present invention is a disposable absorbent pad, which may take various forms, depending upon the particular use contemplated. Thus, it may be a dressing, an underpad, a diaper or the like. It may be designed to absorb and hold body fluids and, as desired, may or may not prevent the passage thereof to the overlying external surface.

The pad may comprise, for example, a top or facing sheet and a bottom or backing sheet, both fabricated from a water-permeable, water dispersible, non-woven fabric bonded together by a polymer of the present invention, as above indicated. The space between the facing sheet and the backing sheet may be filled with an inexpensive readily dispersible disposable absorbent such as, for example, wood pulp or the like. If light bonding of the absorbent is desired, the polymeric composition of the present invention may be used for such purposes.

Alternatively, the backing sheet may comprise a water-impervious sheet such as the laminate of film and low wet strength paper above described, with the paper on the outside or exterior. In all embodiments, the facing sheet and the backing sheet are advantageously bonded together by the simple technique of heat sealing to the thermoplastic polymer adjacent the contacting peripheries.

THE DRAWINGS

The present invention, particularly the composite product embodiments thereof discussed above, may be more clearly understood from the following description read in conjunction with the accompanying drawings, wherein.

It should be understood that the structures are represented in the drawings by graphic symbols and that the drawings are not necessarily to scale. As a result, the representations may depart in certain respects from the actual appearances of the various constructions.

Figure 1:
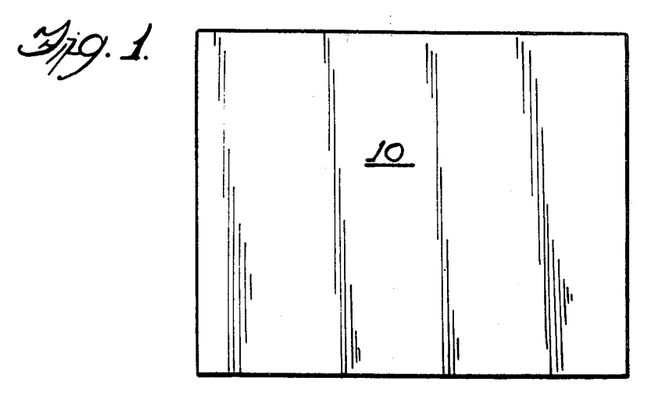
FIG. 1 is a top plan view of a sheet of film prepared from a silane-crosslinked polymeric composition of the present invention.

Referring to FIG. 1, a sheet 10 of silane crosslinked interpolymer of the present invention is cast as a film as described hereinabove, said film typically having a thickness of about 5 mils. In a preferred alkaline labile embodiment, sheet 10 comprises a silane crosslinked copolymer of ethyl acrylate and acrylic acid, 3-(trimethoxysilyl)-propyl methacrylate being the crosslinking monomer. The film contains about 5 percent by weight, based on copolymer, of glycerine and 5 percent by weight, based on copolymer, of lauric acid, whereby the sheet is readily removed from the casting surface and is flexible and conformable to vessels or containers in which it may be placed.

Figures 2, 3, 4, 5, 6:
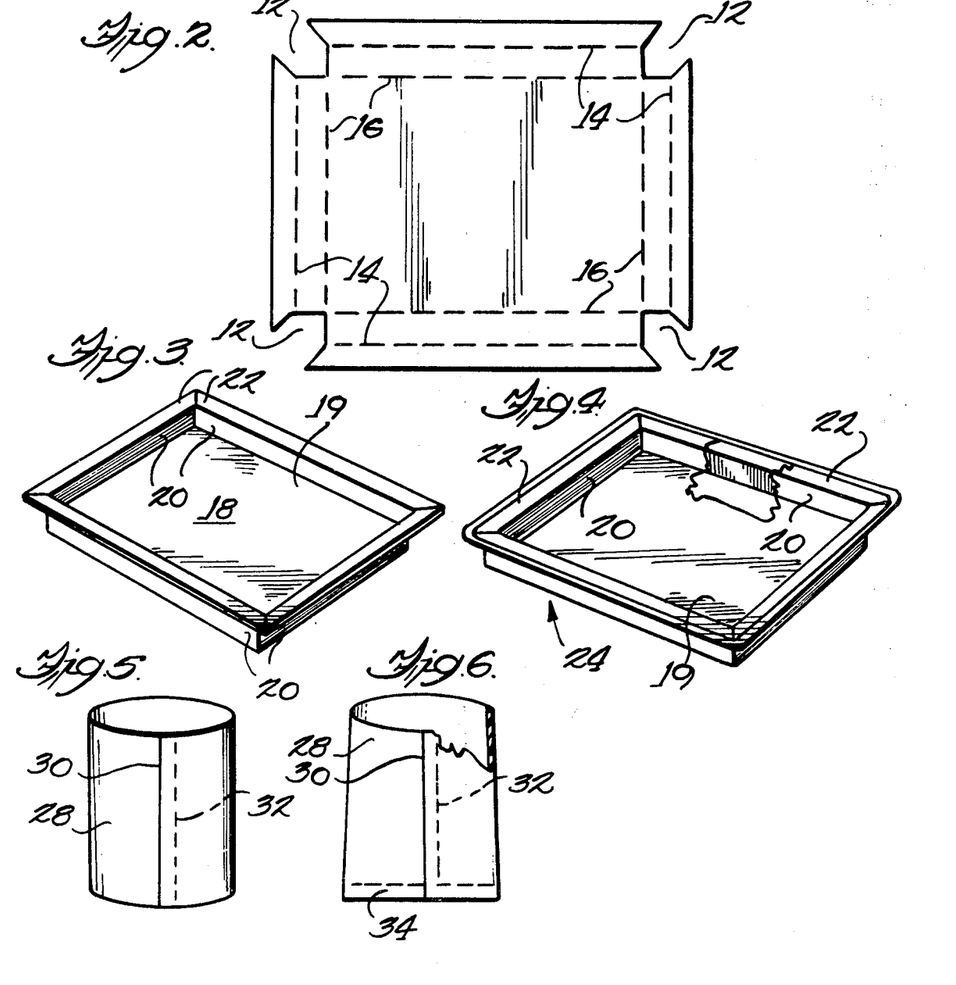
FIG. 2 is a top plan view of the sheet of film of FIG. 1 cut as a blank for forming a bedpan liner.
FIG. 3 is a perspective view of a bedpan liner formed from the sheet of FIG. 2.
FIG. 4 is a perspective view of a bedpan with the liner of FIG. 3 supported therein.
FIG. 5 is an elevation view illustrating a step in the formation of a bag from the film of FIG. 1.
FIG. 6 is an elevation view with parts cut away of the completed disposable bag being formed in FIG. 5.

The four corners of sheet 10 are cut out as indicated by reference numeral 12 in FIG. 2, preparatory to forming the sheet into a bedpan liner. The outer portions are folded along dashed lines 14 and 16 and heat sealed at the edges thereof to form the bedpan liner 18 illustrated in FIG. 3, said liner having bottom wall 19, vertical side walls 20 and horizontal edge portions 22.

In use, liner 18 is inserted into bedpan 24, as illustrated in FIG. 4, the bottom wall, side walls and edge portions of the liner conforming to the corresponding portions of the bedpan. After body exudate is deposited in the bedpan, all that is necessary for disposal is to carry the bedpan to a toilet, deposit the liner with the contents thereof into the toilet, add caustic, and, after 2 to 3 minutes, flush the contents, the liner having dissolved by that time.

FIGS. 5 and 6 illustrate another embodiment of the present invention employing the silane crosslinked interpolymer in film form, a disposable bag such as might be employed for receiving urine. As illustrated in FIG. 5, a sheet of film 28 is folded over, and overlapping edges 30 and 32 are heat sealed to form an open-ended tube. The bag is completed by heat sealing the bottom to form seal 34 shown in FIG. 6.

In like manner, other disposable liners, bags and the like can be prepared, as will be apparent to those skilled in the art who wish to take advantage of the unique water impermeable nature of the film of this invention and its ready disposability in aqueous alkaline solutions. Numerous composite products may also be prepared as illustrated in the ramaining drawings.

Figure 7:
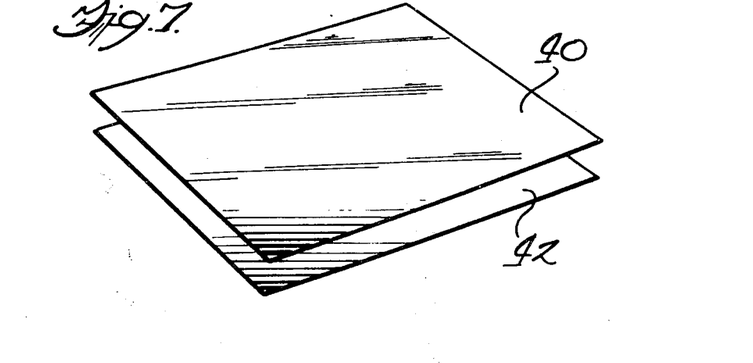
FIG. 7 is a perspective view illustrating a polymeric film and a paper web which are subsequently laminated to form a composite structure of the present invention.
Figure 8:
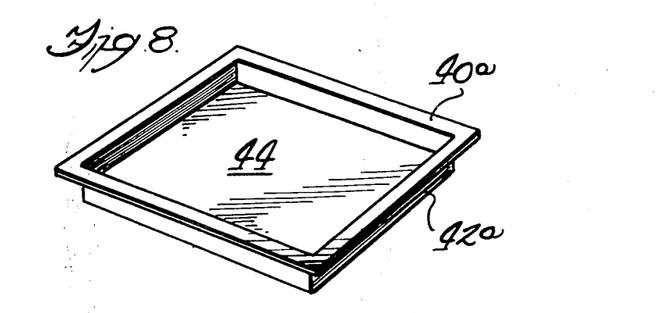
FIG. 8 is a perspective view illustrating a bedpan prepared from the composite structure formed by laminating the film and paper of FIG. 7.

Referring to FIG. 7, a film 40 of the present invention may be laminated by heat and pressure to low wet strength paper 42, typical laminating conditions being a temperature of 50°-60° C, a pressure of 50 psi, and a laminating dwell time of one second. The laminated structure is cut and fabricated into a bedpan 44 comprising inner film 40a and outer paper 42a, as illustrated in FIG. 8. Bedpan 44 may optionally be self-supporting, in which case the film and paper thicknesses and other characteristics are selected to achieve the requisite strength and stiffness. As shown in FIG. 8, the paper layer 42a is disposed on the exterior so that the moisture-impermeable barrier provided by film 40a separates the moisture sensitive paper and the liquid contents of the bedpan.

Figures 9, 10:
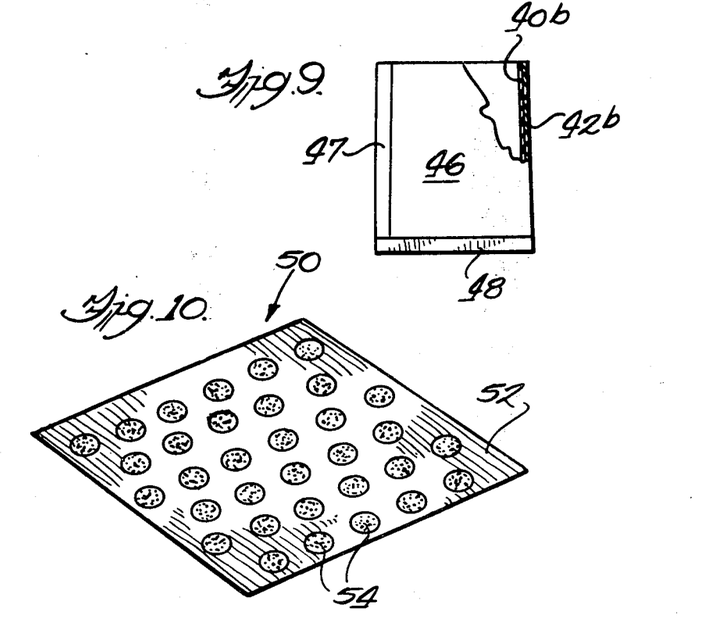
FIG. 9 is an elevation view with parts cut away illustrating a disposable bag prepared from the composite structure formed by laminating the film and paper of FIG. 7.
FIG. 10 is a perspective view illustrating a nonwoven fabric prepared using the polymeric composition of the present invention as a binder therefor.

Likewise, a urine collection bag similar to that of FIG. 6 may also be fabricated from the film-paper composite, as illustrated in FIG. 9. Bag 46 is heat sealed together with film 40b of the laminate on the interior and the low wet strength paper 42b on the exterior, the side seal (not in overlapping relationship) being indicated by reference numeral 47 and the bottom seal being indicated by reference numeral 48. Film 40b prevents contact between the liquid contents and the low wet strength paper. The dry strength of the paper thus minimizes extensibility and otherwise strengthens the bag.

Referring to FIG. 10, there is illustrated a nonwoven fabric 50 which comprises water dispersible, biodegradable non-woven fibers 52 "spot bonded" together by a plurality of discrete polymeric deposits 54, comprising a preferably alkaline soluble, silane crosslinked interpolymer of the present invention. Similarly, in FIG. 11 there is illustrated a non-woven fabric 56 which comprises water dispersible, biodegradable non-woven fibers 58 bonded together by discrete polymeric deposits 60 which are located and configured in the articulated multisegmental binder pattern of the aforementioned U.S. Pat. No. 2,705,687.

Figure 11:
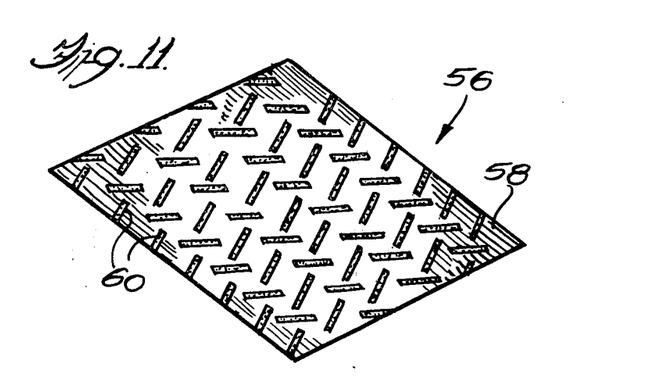
FIG. 11 is a perspective view similar to FIG. 10 but illustrating a different binder pattern for the polymer deposits.

As already indicated, the fibers of fabrics 50 and 56 may be "unoriented" or "oriented", e.g., substantially "parallelized", as desired for specific applications. Instead of the preferred "spot bonding", the silane-crosslinked polymeric binder may be distributed throughout the fiber web. All embodiments of the non-woven fabrics 50 and 56 are, however, completely disposable and flushable, as contemplated by the present invention.

Figure 12:
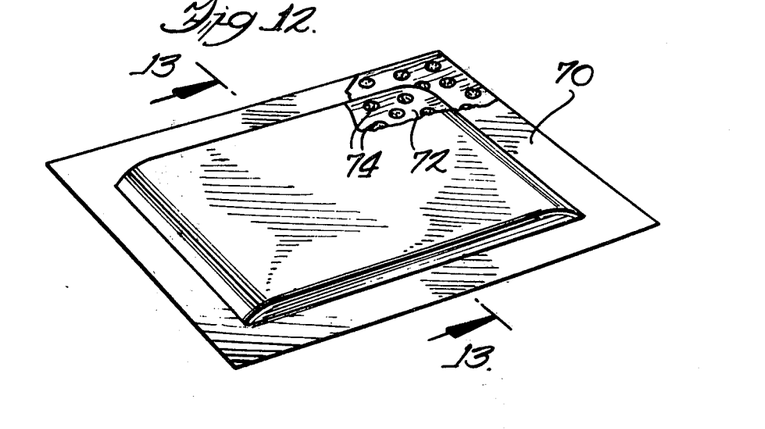
FIG. 12 is a perspective view with parts cut away of an absorbent pad fabricated in part from the composition of the present invention.
Figure 13:
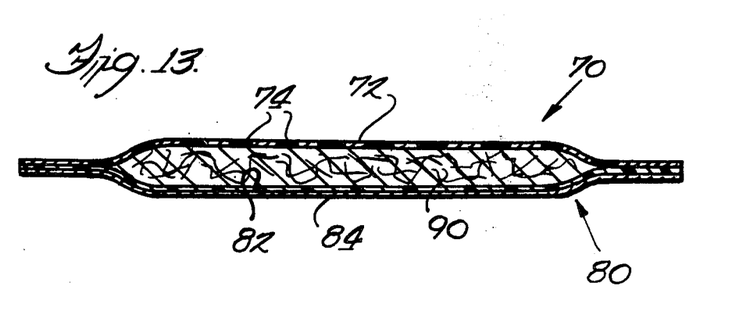
FIG. 13 is a sectional view along the line 13—13 of FIG. 12.

A completely-disposable absorbent pad suitable for use as an underpad, diaper or the like is illustrated in FIGS. 12 and 13. The top or facing sheet 70 may be prepared, for example, from the non-woven fabrics already described in connection with FIGS. 10 and 11. While the individual non-woven fibers and polymeric deposits may not be readily detectable to the casual viewer, they are indicated in the cutaway portions of FIG. 12 by reference numerals 72 and 74, respectively, solely for purposes of illustration. Likewise, while the fiber layer 72 and polymeric deposits 74 are shown discretely for purposes of illustration in the sectional drawing of FIG. 13, the deposits are actually intermingled with the fibers at the deposit locations.

Non-woven fabric 70 is laminated at its periphery, e.g., by application of heat and pressure, to the bottom or backing sheet 80 comprising a film-paper laminate similar to that described in connection with FIGS. 7-9. The film portion 82 of laminate 80 comprises a polymeric composition of the present invention and is disposed on the interior and the low wet strength 84 is disposed on the exterior. The space between facing sheet 70 and backing sheet 80 is filled with an inexpensive, water-dispersible absorbent 90 such as wood pulp or the like. If bonding of absorbent 90 is desired, the polymeric composite of the present invention may be added thereto for such purposes.

In use, body exudates pass through permeable facing sheet 70 and saturate absorbent 90. No moisture penetrates backing sheet 80 because film 82 is a water barrier. The paper outer layer 84 provides dry strength to the composite and non-blocking characteristics to the surface. The entire structure, however, is readily disposable and flushable in accordance with the present invention.

EXAMPLES

The present invention will be more clearly understood from the following specific examples of certain embodiments which have already been generally described and illustrated hereinabove.

EXAMPLE 1 — ALKALINE SOLUBLE FILM

A polymerization vessel was fitted with a condenser, stirrer, thermometer and nitrogen inlet tube. The vessel was charged with 280 parts by weight of ethyl acrylate, 120 parts of acrylic acid, 4.0 parts of 3-(trimethoxysilyl)-propyl methacrylate, 406 parts of ethyl acetate and 138 parts of isopropanol. The solution was stirred and swept with nitrogen while raising the temperature to 75° C. Then 1.0 part of 2,2-azobis-(2-methylpropionitrile) was added and the nitrogen flow discontinued. Polymerization began and the solution refluxed vigorously at 86° C. After the exothermic polymerization had subsided, stirring and heating of the reaction mixture at 80° C was continued for 3.5 hours. The solution was then diluted with 388 parts of isopropanol and cooled. Solids content of the solution was 30%.

To 300 parts of the 30% solution were added 4.5 parts of glycerine plasticizer and 0.45 part of dibutyl tin di-2-ethylhexoate catalyst. A two-coat film was cast on siliconed paper, with air drying between coats. After air drying the second coat, the film was further dried in an oven at 75° C for 15 minutes and then stripped from the siliconed paper as a single film.

The resulting film was found to be about 5 mils in thickness. When used as the liner in pans, dishes or bags, it holds water without leaking for more than 24 hours. It is soluble in alkaline solutions and flushable in conventional toilet systems.

The following table summarizes the time required for swatches fo the film to dissolve in various base solutions.

| Reagent Wt. % | Estimated pH | Time to Dissolve, Minutes |
|---|---|---|
| SODIUM HYDROXIDE | | |
| 8.0 | 14.3 | 5 |
| 4.0 | 14.0 | 5 |
| 2.0 | 13.7 | 4 |
| 1.0 | 13.4 | 4 |
| 0.5 | 13.1 | 5 |
| 0.25 | 12.8 | 18 |
| SODIUM CARBONATE | | |
| 10.0 | 12.1 | 9 |
| 5.0 | 12.0 | 8 |
| 2.5 | 11.8 | 8 |
| 1.0 | 11.6 | 12 |
| AMMONIUM HYDROXIDE | | |
| 10.0 | 12.0 | 10 to 15 |
| 5.0 | 11.8 | 10 to 15 |

EXAMPLE 2 — ALKALINE SOLUBLE FILM

The polymerization of Example 1 was repeated using the crosslinking monomers shown in the following table. Essentially quantitative conversions of monomer to polymer were obtained in each case as shown by the nonvolatile solids content of the solution after polymerization.

Crosslinking of the respective 30% solids solutions was effected by adding 0.5% by weight, based on polymer, of dibutyl tin di-2-ethylhexoate catalyst to the polymer solution, casting the solution on polyethylene, and drying first at room temperature and then at 75° C for 15 minutes. Gel content of the crosslinked polymers was measured by dissolving crosslinked film in ethyl acetate and screening the insoluble material from the solutions, the solutions having been prepared by allowing 0.5 gram samples of polymer to stand at room temperature for 48 hours in 50 ml. of ethyl acetate. The results are as follows:

| Crosslinked Agent | Parts* | Solids, Wt. % | Gel, Wt. % | Water Barrier properties of 2-mil Films |
|---|---|---|---|---|
| 3-(trimethoxysilyl)-propyl methacrylate | 0 | 29.9 | None | Poor |
| | 0.25 | 29.6 | — | Poor |
| | 0.50 | 29.9 | — | Poor |
| | 1.0 | 29.6 | 64. | Excellent |
| Allyl Triethoxysilane | 1.0 | 30.0 | 43. | Poor |
| | 2.0 | 29.7 | 71. | Poor |
| Vinyl triethoxysilane | 1.0 | 29.7 | 53. | Poor |
| Vinyl triacetoxysilane | 1.0 | 29.9 | 48. | Poor |

*Parts per 100 parts by weight of ethyl acrylate and acrylic acid

EXAMPLE 3 — ALKALINE SOLUBLE FILM

A polymer solution of 30% solids content was prepared as in Example 1. A portion (150 parts by weight) of the solution was mixed with 0.22 part of dibutyl tin di-2-ethylhexoate and cast as a film on polyethylene-coated paper. Casting was regulated so as to give a film thickness after drying of about 2 mils. The film was heated for 15 minutes at 75° C after air drying at room temperature for an hour. Under conditions of 25 to 50% relative humidity, this film cracks when flexed.

Another portion of the same 30% solids solution was mixed with 0.22 part of dibutyl tin di-2-ethylhexoate, 2.25 parts of glycerine and 2.25 parts of lauric acid. A 2-mil film was cast and dried from this solution also. It was found that this film is removed more easily from the polyethylene substrate and that it has no tendency to crack when flexed under conditions of 25 to 50% relative humidity. The film has excellent impermeability to water. Portions of the film dissolved readily in 0.5% sodium hydroxide water solutions.

EXAMPLE 4 — ACID SOLUBLE FILM

A 5-liter, 3-neck flask was fitted with a reflux condenser, mechanical stirrer, thermometer and nitrogen inlet tube. The following chemicals were charged to the flask:

| | | |
|---|---|---|
| Ethyl acrylate | 350 | grams |
| N-isopropylacrylamide | 150 | " |
| N,N-dimethylaminoethyl methacrylate | 500 | " |
| 3-(trimethoxysilyl)-propyl methacrylate | 10 | " |
| Ethyl acetate | 1000 | " |

The flask was immersed in an electrically-heated oil bath and the contents stirred and swept with a slow stream of nitrogen. The solution reached a temperature of 75° C in 30 minutes, at which point 2.55 grams of 2,2'-azobis-(2-methylpropionitrile) were added and the nitrogen turned off. The temperature then rose to 89° C, at which point polymerization proceeded smoothly as the solvent refluxed. After the vigorous reaction subsided, the temperature was allowed to decline to 75°–80° C. The reaction mixture was maintained at this temperature and stirred until the total reaction period amounted to 4 hours. The reaction mixture was then cooled and found to have a polymer content of 48.3%.

A 282 gram portion of the reaction mixture was diluted with 59 grams of isopropanol and 59 grams of toluene, and 0.68 gram of dibutyl tin di-2-ethylhexoate dissolved in 2 ml. of toluene was added. The solution was then spread in a smooth layer on silicone-coated paper. The film was dried first at room temperature, then at 60° C, and finally for an hour at 75° C. The thickness of the dried film was 5 to 6 mils. A second coat was applied and dried in the same way, bringing the film thickness to the 10 to 12-mil range. The film was then stripped from the siliconed paper.

In a dry state, the film is clear, flexible and has a surface which is slightly cohesive. Under humid conditions the surface becomes a little more cohesive due to moisture absorption. The film will block to itself on long standing and is stored with an interliner, e.g., siliconed paper.

The film is insoluble in urine and in aqueous solutions which are not strongly acid. It rapidly breaks up and dissolves in hydrochloric acid of 4 to 6 normal concentration (12 to 18% HCl).

Urine bags having holding capacities of about 125 ml. were made from the film. If a single 10 to 12-mil thickness was used to make the bag, the wet film in the filled bag stretched enough to cause breakage after 12 to 18 hours. A slower rate of stretching occurred if two 10 to 12-mil thickness of film were used to make the bag, a two-layer prototype holding urine for 24 hours without pronounced stretching. But, ultimately, stretching of the double layer bag became just as bad as with a single layer bag. The dry film shows no stretching at all under a 125-gram dry load.

EXAMPLE 5 — ADDITIONAL ACID SOLUBLE FILMS

A series of acid soluble films was prepared substantially as described in Example 4, except that the proportions of ethyl acrylate ("EA"), dimethylaminoethyl methacrylate ("DMAEMA"), N-isopropylacrylamide ("NIPAM") and 3-(trimethoxysilyl)-propyl methacrylate ("3-TPM") were varied. Properties of the films, which were cured for 1 hour at 75° C with 0.5% by weight, based on polymer, of dibutyl tin di-2-ethylhexoate, are set forth in the following table.

| | Polymer Composition, Parts by Weight | | | | |
|---|---|---|---|---|---|
| Run | EA | DMAEMA | NIPAM | 3-TPM | Properties of Cured Film |
| 1 | 75 | 25 | — | 0.4 | Tacky, flexible cohesive. |
| 2 | 50 | 50 | — | 0.4 | Tacky, very flexible. |
| 3 | 25 | 50 | 25 | 0.4 | Stiff and boardy. Disintegrates and dissolves in 2NHCl within a few minutes. Insoluble in distilled water and 1.5% NaCl. |
| 4 | 52.5 | 25 | 22.5 | 1.0 | In 2NHCl film swelled and became thin and soft but did not dissolve. Insoluble in distilled water and 1.5% NaCl. |
| 5 | 52.5 | 25 | 22.5 | 0.5 | In 2NHCl film swelled strongly and became very soft, dissolving completely in about 4 hours. Film was insoluble in distilled water and 1.5% NaCl. |
| 6 | 35 | 50 | 15 | 2.0 | Reaction mixture gelled during polymerization. |
| 7 | 35 | 50 | 15 | 1.0 | Flexible film having surfaces slightly cohesive. In 2NHCl film disintegrates in about 15 minutes and dissolves completely on standing overnight. Film is insoluble in distilled water and 1.5% NaCl. |
| 8 | 35 | 50 | 15 | 0.5 | Like film of Run 7 in appearance and feel. In 2NHCl it dissolved completely in less than one hour. Film was insoluble in water but became very soft, spongy and highly swollen after two days. In 1.5% NaCl the film became softer than film of Run 7. |
| 9 | 35 | 50 | 15 | 0.25 | Like film of Run 7 in appearance and feel. In 2NHCl it disintegrated in 10 to 15 minutes and dissolved completely in about 20 minutes. Film was insoluble in water but became very soft, spongy and highly swollen after two days. In 1.5% NaCl the film became softer than films of Runs 7 and 8. |
| 10 | — | 80 | 20 | 2.0 | Reaction mixture gelled during polymerization. |

-continued

| Run | Polymer Composition, Parts by Weight | | | | Properties of Cured Film |
| --- | --- | --- | --- | --- | --- |
| | EA | DMAEMA | NIPAM | 3-TPM | |
| 11 | — | 80 | 20 | 1.0 | Film was a little less flexible than film of Run 7. In 2NHCl it disintegrated after soaking for a few minutes and dissolved completely within 30 minutes. In distilled water alone the film dissolved on standing overnight. In 1.5% NaCl the film did not dissolve but became swollen and too weak to handle. |

The data in the foregoing table indicate that N-isopropylacrylamide eliminates surface tack and that 50% dimethylaminoethyl methacrylate is about the right amine composition. Polymers with 25% dimethylaminoethyl methacrylate are not sufficiently acid soluble, while those containing 80% dimethylaminoethyl methacrylate are too hydrophilic, dissolve in water, and therefore are not water barriers.

The data also indicate that optimum crosslink density is obtained with about 1.0 part of 3-(trimethoxysilyl)-propyl methacrylate per 100 parts of other monomers. Less silane leads to polymers which are too water-sensitive and which lack wet strength. If the silane concentration is as high as 2.0 parts per 100 parts of monomer, gelation occurs during polymerization.

The effect of silane concentration on polymer solubility is shown from the following data obtained on the polymers from Runs 7, 8 and 9. In each of these runs the other monomers are 35 parts or ethyl acrylate, 15 parts of N-isopropylacrylamide and 50 parts of dimethylaminoethyl methacrylate, as indicated in the previous table.

| Source of Polymer | Silane, pts./100 | Solubility, % | | |
| --- | --- | --- | --- | --- |
| | | In Water | In Toluene | In Ethyl Acetate |
| Run 7 | 1.0 | 0 | 23 | 23 |
| Run 8 | 0.5 | 0 | 37 | 36 |
| Run 9 | 0.25 | 1 | 66 | 67 |

Highly crosslinked, water-insoluble, hydrophilic polymers are hydrogels, if crosslinking density is not so high as to prevent imbibition of water. Hydrogels imbibe water, reaching a certain equilibrium water absorption. The equilibrium depends on polymer composition, crosslink density, composition of the aqueous swelling liquid, and temperature. For example, the polymer from Run 7 has an equilibrium water absorption at room temperature in 1.5% sodium chloride solution of 31 to 35% and the polymer from Run 8, 39 to 44%.

EXAMPLE 6 — ALKALINE-LABILE FILM AND PAPER COMPOSITE

A 30% solids solution of polymer was prepared as in Example 1. A thin coat of this solution was cast on polyethylene-coated paper. After partial drying of the solvent from the film in air at room temperature, or slightly above, a layer of 3-mil-thick, high-absorbency, no wet strength tissue paper was smooth onto the surface of the film. The paper had a dry tensile strength of 300 g./inch-width in the machine direction and 150 g./inch-width in the cross machine direction. The paper bonded firmly to the film surface as drying was completed at room temperature and by a final 15 minute treatment in an oven at 75° C. Casting of the film was regulated so that the dry film thickness was about 2 mils. Thus, the final laminate consists of about 2 mils of film and 3 mils of tissue paper. The laminate is readily stripped from the polyethylene substrate.

The 5-mil film-paper laminate is much easier to handle than a 2-mil free film. The paper surface of the laminate prevents excessive stretching of the thin film and provides a non-blocking surface on one side.

A circular piece of the laminate, 8 inches in diameter, was formed into a urine collection bag of about 125 cc. capacity by heat sealing the film edges around the periphery of a 2.5-inch-diameter rigid ring. The film is readily heat sealable to itself. The paper surface was disposed on the outside or exterior of the bag, so that it would remain dry and contribute strength to the urine-filled bag.

Bags of this type held urine without leaking for more than 24 hours. A similar bag formed of 2-mil free film without the paper fibers does not have sufficient strength when wetted to hold such weight of urine.

The film part of the film-paper laminate dissolves completely in 0.5 weight percent sodium hydroxide solution within two minutes after immersion.

EXAMPLE 7 — ALKALINE-LABILE, NON-WOVEN FABRIC

A 30% solids solution of polymer was prepared as set forth in Example 1. A portion of this solution was diluted to 5% solids with a solvent comprising 88 weight percent isopropanol and 12% ethyl acetate. A web of 75 weight percent wood pulp and 25% 1.5 denier rayon, supported on a screen, was saturated with the 5% polymer solution. The excess solution was filtered from the web with suction, leaving the wet web with a 168% increase in weight due to pickup of the solution. The wet web was dried in a hot air oven at about 120° F (49° C) and finally given a one-minute heat treatment at 300° F (149° C).

An 8.4% add-on of polymer resulted from this treatment. The bonded web is perfectly stable in aqueous solutions having pH values less than about 9. The web disintegrates completely within five minutes when immersed in a 1% aqueous sodium hydroxide solution.

The above experiment was repeated using a polymer solution of 2.5% solids concentration to impregnate the web. Wet pickup was 166%, and dry polymer add-on was 4.2%. This web is completely disintegrated after three minutes immersion in 1% sodium hydroxide solution.

EXAMPLE 8 — ALKALINE-LABILE ABSORBENT PAD

An alkaline-labile film and paper composite was prepared as in Example 6 and heat sealed adjacent its periphery to an alkaline-labile non-woven fabric prepared as in Example 7, with an absorbent batt of wood pulp fibers between the two layers, as illustrated in FIGS. 11 and 12. The result was a self-contained, completely disposable absorbent pad which effectively retains the absorbed liquid waste and prevents its passage to the exterior surface. The entire unit is toilet flushable after establishing the requisite alkaline conditions, i.e., an alkaline pH, preferably above 12, in the toilet bowl.

From the above description, drawings and examples, it is apparent that the objects of the present invention have been achieved. While only certain embodiments have been described or illustrated, many alternative modifications and equivalents will be apparent from the above description to those skilled in the art. These and other alternatives and equivalents are considered to be within the spirit scope of the present invention.

Having thus described my invention, what I desire to secure by Letters Patent and hereby claim is:

1. A laminated structure comprising a film of a film-forming polymeric composition having water-barrier properties at neutral pH's in the range of between about 4.5 and about 8.5 and solubilizable at a pH substantially outside said neutral pH range, said composition comprising a silane-crosslinked interpolymer of about 0.5 to 5 parts by weight of a first monomer selected from the group consisting of the alkyl acrylates wherein the alkyl group has from one to eight carbon atoms, and about 1 part by weight of a second monomer selected from the group consisting of acrylic acid, methacrylic acid, fumaric acid, maleic acid, maleic anhydride, itaconic acid, dimethylaminoethyl acrylate, dimethylaminoethyl methacrylate, diethylaminoethyl acrylate, diethylaminoethyl methacrylate, tert.-butylaminoethyl acrylate and tert.-butylaminoethyl methacrylate, and about 0.9 to 1.5% by weight, based on the combined weight of said first and second monomers, of a crosslinking monomer selected from the group consisting of the silane monomers having the structural formula:

wherein:
R is selected from the group consisting of $CH_3-$, $CH_3CH_2-$, $CH_3CH_2O-$;
$R_1$ and $R_2$ are each selected from the group consisting of $CH_3-$ and $CH_3CH_2-$;
$R_3$ is selected from the group consisting of H, $CH_3-$ and $CH_3CH_2-$;
and $n$ is 0 or a positive integer not greater than 8; said film having a thickness in the range of about 1 to 20 mils and being laminated at least on one side of a water dispersible non-woven fiber web having low wet strength.

2. The laminated structure of claim 1 wherein said first monomer is ethyl acrylate and said silane monomer is selected from the group consisting of 3-(trimethoxysilyl)-propyl methacrylate and 3-(trimethoxysilyl)-propyl acrylate.

3. The laminated structure of claim 2 wherein said second monomer is selected from the group consisting of acrylic acid, methacrylic acid, fumaric acid, maleic acid, maleic anhydride and itaconic acid.

4. The laminated structure of claim 2 wherein said second monomer is selected from the group consisting of dimethylaminoethyl acrylate, dimethylaminoethyl methacrylate, diethylaminoethyl acrylate, diethylaminoethyl methacrylate, tert.-butylaminoethyl acrylate and tert.-butylaminoethyl methacrylate.

5. The laminated structure of claim 3 wherein said second monomer is acrylic acid.

6. The laminated structure of claim 4 wherein said second monomer is dimethylaminoethyl methacrylate.

7. The laminated structure of claim 6 wherein said polymeric composition further comprises a tack-diminishing quantity of N-isopropylacrylamide.

8. The laminated structure of claim 1 wherein said polymeric composition further comprises about 1 to 20% by weight, based on the weight of said interpolymer, of a humectant-type plasticizer.

9. The laminated structure of claim 8 wherein said humectant-type plasticizer is selected from the group consisting of glycerin, diethylene glycol, triethylene glycol, propylene glycol, dipropylene glycol and tripropylene glycol.

10. The laminated structure of claim 1 wherein said polymeric composition further comprises about 1 to 20% by weight, based on the weight of said interpolymer, of a plasticizer having release-agent properties.

11. The laminated structure of claim 10 wherein said plasticizer is selected from the group consisting of lauric acid, myristic acid and palmitic acid.

12. The laminated structure of claim 1 wherein said polymeric composition has water-barrier properties at pH's below about 8.5 and is solubilizable at pH's above about 9, said composition comprising a silane-crosslinked interpolymer of about 1.5 to 4 parts by weight of a first monomer selected from the group consisting of the alkyl acrylates wherein the alkyl group has from one to eight carbon atoms, and about 1 part by weight of a second monomer selected from the group consisting of acrylic acid, methacrylic acid, fumaric acid, maleic acid, maleic anhydride and itaconic acid, and about 0.9 to 1.5% by weight, based on the combined weight of said first and second monomers, of a crosslinking monomer selected from the group consisting of the silane monomers having the structural formula:

wherein:
R is selected from the group consisting of $CH_3-$, $CH_3CH_2-$, $CH_3O-$ and $CH_3CH_2O-$;
$R_1$ and $R_2$ are each selected from the group consisting of $CH_3-$ and $CH_3CH_2-$;
$R_3$ is selected from the group consisting of H, $CH_3-$ and $CH_3CH_2-$;
and $n$ is 0 or a positive integer not greater than 8.

13. The laminated structure of claim 1 wherein said web comprises cellulosic fibers.

14. The laminated structure of claim 1 in the form of a vessel, for retaining fluids having neutral pH's in the range of about 4.5 to 8.5, the web portion of the structure being disposed on the exterior of said vessel.

15. The laminated structure of claim 1, further comprising, on the side of said film opposite said low wet strength web, and heat sealed at least to peripheral portions of said film, a moisture permeable, water-dispersible, non-woven fabric comprising a web of overlapping, intersecting fibers bonded together with a polymeric composition having water-barrier properties at neutral pH's in the range of between about 4.5 and about 8.5 and solubilizable at a pH substantially outside said neutral pH range, said composition comprising a silane-crosslinked interpolymer of about 0.5 to 5 parts by weight of a first monomer selected from the group consisting of the alkyl acrylates wherein the alkyl group has from one to eight carbon atoms, and about 1 part by weight of a second monomer selected from the group consisting of acrylic acid, methacrylic acid, fumaric acid, maleic acid, maleic anhydride, itaconic acid, dimethylaminoethyl acrylate, dimethylaminoethyl methacrylate, diethylaminoethyl acrylate, diethylaminoethyl methacrylate, tert.-butylaminoethyl acrylate and tert.-butylaminoethyl methacrylate, and about 0.9 to 1.5% by weight, based on the combined weight of said first and second monomers, of a crosslinking monomer selected from the group consisting of the silane monomers having the structural formula:

wherein:
R is selected from the group consisting of $CH_3-$, $CH_3CH_2-$, $CH_3O-$ and $CH_3CH_2O-$;
$R_1$ and $R_2$ are each selected from the group consisting of $CH_3-$ and $CH_3CH_2-$;
$R_3$ is selected from the group consisting of H, $CH_3-$ and $CH_3CH_2-$;
and $n$ is 0 or a positive integer not greater than 8.

16. The laminated structure of claim 15 further comprising an absorbent matrix of non-woven fibers sandwiched between said film and said moisture permeable, water-dispersible, polymer bonded, non-woven fabric.

* * * * *

UNITED STATES PATENT AND TRADEMARK OFFICE
CERTIFICATE OF CORRECTION

PATENT NO. : 4,062,451
DATED : December 13, 1977
INVENTOR(S) : Robert J. Gander

It is certified that error appears in the above-identified patent and that said Letters Patent are hereby corrected as shown below:

Col. 7, line 28 - "forms" should be --form--

Col. 10, line 34 - "ramaining" should be --remaining--

Col. 12, line 17 - "swatches fo the" should be --swatches of the--

Col. 15, line 30 - "35 parts or ethyl" should be --35 parts of ethyl--

Col. 17, line 11 - "spirit scope" should be --spirit and scope--

Col. 17, line 12 - "whan I desire" should be --what I desire--

Col. 17, line 43 - "$CH_3CH_2-$, $CH_3CH_2O-$;" should be --$CH_3CH_2-$, $CH_3O-$ and $CH_3CH_2O-$;--

Signed and Sealed this

Twenty-eighth Day of July 1981

[SEAL]

Attest:

GERALD J. MOSSINGHOFF

*Attesting Officer*   *Commissioner of Patents and Trademarks*